United States Patent [19]

Boyd

[11] Patent Number: 4,583,542

[45] Date of Patent: Apr. 22, 1986

[54] HEMORRHOIDAL PESSARY

[76] Inventor: Zane R. Boyd, 120 S. Maize Rd. #12, Wichita, Kans.

[21] Appl. No.: 659,766

[22] Filed: Oct. 11, 1984

[51] Int. Cl.$^4$ ............................................ A61M 29/00
[52] U.S. Cl. ........................................ 128/341; 128/67
[58] Field of Search .................. 128/341, 56, 132 D, 128/67, 79

[56] References Cited

U.S. PATENT DOCUMENTS

| 988,120 | 3/1911 | Lott | 128/341 |
|---|---|---|---|
| 1,534,756 | 4/1925 | Austin | 128/341 |
| 1,877,766 | 9/1932 | Kennedy | 128/341 |
| 2,017,334 | 10/1935 | Ackerman | 128/341 |
| 2,468,348 | 4/1949 | Shore | 128/341 |
| 2,721,549 | 10/1955 | Ferraro | 128/341 |
| 3,894,539 | 7/1975 | Tallent | 128/341 |

FOREIGN PATENT DOCUMENTS

| 970225 | 6/1948 | France | 128/341 |
|---|---|---|---|
| 139914 | 3/1920 | United Kingdom | 128/341 |
| 233903 | 5/1925 | United Kingdom | 128/341 |

Primary Examiner—John J. Wilson
Assistant Examiner—John G. Weiss
Attorney, Agent, or Firm—Edward L. Brown, Jr.

[57] ABSTRACT

A hemorrhoidal device insertable in the rectum for treatment of hemorrhoids by the application of gentle pressure against the dilated veins, the device including a body of soft pliable plastic having a tapered head portion with a circumferential shoulder which terminates at the shaft portion of the device, the end of the shaft portion terminating in an outwardly standing flange. Concentrically molded within the body of the device is a stiffener member extending the substantial length of the device for providing sufficient rigidity for insertion and tensile strength for removal.

10 Claims, 5 Drawing Figures

HEMORRHOIDAL PESSARY

BACKGROUND OF THE INVENTION

Hemorrhoids, also referred to as piles, is a condition whereby the veins of the anal canal are dilated, similar to varicose veins in the leg. In extreme cases these veins become distended and extend out of the rectal opening which condition may be accompanied by pain and bleeding.

Various methods of treating hemorrhoids have been tried in the past including the usage of ointments, supports, and truss structures, as set forth in U.S. Pat. Nos. 115,285 issued May 30, 1871 to Dithridge; 812,679 issued Feb. 13, 1906 to Reimanns; 2,658,599 issued Sept. 29, 1953 to Bell; 3,712,300 issued Jan. 23, 1973 to Davidowitz; 4,263,914 issued Apr. 28, 1981 to Pawlak.

However, none of these methods or structures have been particularly successful. In severe cases, surgery for the removal of the vein has been utilized but this is not necessarily a permanent cure, and the procedure is a painful ordeal.

DESCRIPTION OF THE PRIOR ART

The U.S. Pat. No. 2,653,599 mentioned above is on a similar device made from flexible material, however, the particular shape of the present invention is substantially different from the above reference. By reason of the stiffener in the present invention, a much softer material can be utilized thereby vastly improving the comfort level of the wearer.

U.S. Pat. Nos. 115,285 and 812,679 are both constructed of totally rigid materials even though they teach a somewhat similar structure and would be most uncomfortable for a user for an extended period.

U.S. Pat. No. 3,712,300 is also a rigid device without a pronounced shoulder for retention by the sphincter muscles. The device in this patent requires the additional structure of a waist band and support strap to retain the device in the anal canal.

U.S. Pat. No. 4,263,914 teaches a rigid device without the pronounced shoulder utilized to massage the hemorrhoids rather than a static application as in the present invention. Prolonged placement of any rigid device would be overly uncomfortable to a user.

The present state of the art does not include any device having sufficient softness, including the patent to Bell mentioned above, to allow a user to wear the device for extended periods while walking, sitting or performing other normal ambulatory functions.

SUMMARY OF THE INVENTION

The device of the present invention is constructed of a very soft plastic or rubber substance which because of its pliability can be worn by the user for extended periods of time with a much improved comfort level over some of the rigid devices mentioned in the patents above.

It is therefore the principal object of the present invention to provide a hemorrhoidal device for insertion in the rectum which is formed from a very soft pliable material to minimize the pain to the patient while providing gentle pressure against the dilated veins.

Another object of the present invention is to provide a hemorrhoidal pessary of soft pliable material which has a sufficient longitudinal rigidity and tensile strength for insertion and removal.

A further object of the present invention is to provide a hemorrhoidal device which is comfortable for the user to wear while being simple in design and inexpensive to manufacture.

These and other objects will be readily apparent upon study of the following specification and the accompanying drawings.

DESCRIPTION OF THE PREFERRED EMBODIMENT

Figure 1:
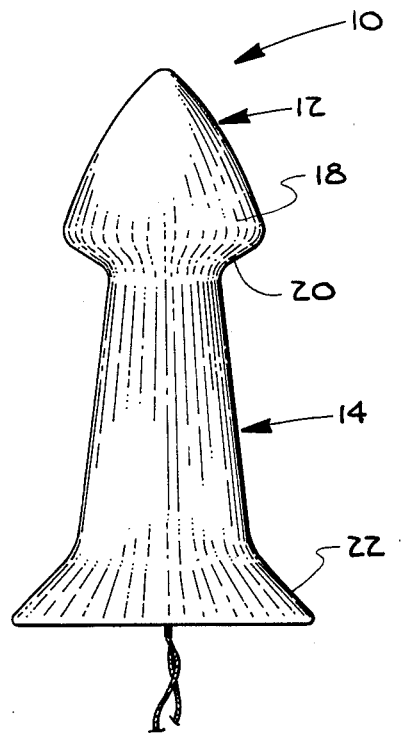
FIG. 1 is an elevational view of the hemorrhoidal pessary.

Referring now to the drawings in detail and more particularly to FIGS. 1 and 3, the hemorrhoidal pessary, also referred to as hemorrhoidal device, is generally described by reference numeral 10. The pessary 10 comprises a head 12 and a shaft 14, the head having a tapered shape from its nose end 16 back to a corona portion 18. Along the rear portion of the head 12 is a circumferential shoulder 20 which joins with the shaft portion 14 of the device 10. At the juncture with the head 12, the shaft diameter is substantially less than that of the corona portion 18 but tapers outward as the shaft extends away from the head. The end of the shaft 14 terminates in an outwardly extending flange 22.

Figures 2, 5:
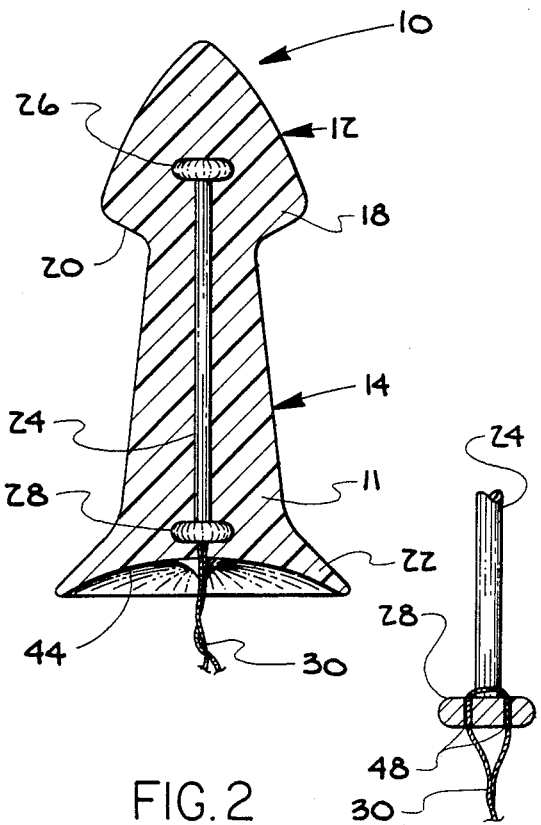
FIG. 2 is a longitudinal section.
FIG. 5 is a partial section of the end of the stiffener member.

Molded within the center of the device 10 is a stiffener member 24, as best seen in FIG. 2, which can be made of metal or some form of rigid plastic. Stiffener 24 includes two enlarged end portions or buttons 26 and 28, which increase the surface contact area between the soft body 11 of the device and the stiffener member 24. Lower end portion 28, shown in detail in FIG. 5, includes two holes 48 therethrough for insertion and passage of a removal string 30 which extends outside the soft body 11 of the device. Various other types of handle means could be utilized in place of string 30, such as some type of handle extension extending outwardly from end portion 28. The stiffener member 24 also adds longitudinal stiffness to the soft body 11 to prevent the head from separating from the shaft during removal from the anal canal. Button 28 provides the additional function of allowing the person inserting the hemorrhoidal device 10 a flat rigid area for applying pressure to a device which is otherwise quite flexible.

Figure 3:
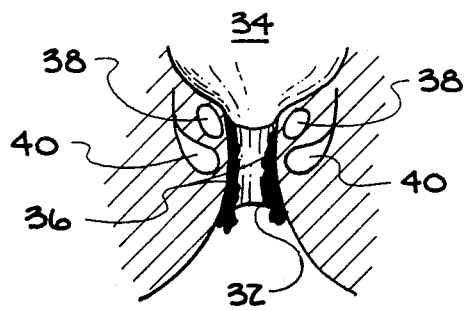
FIG. 3 is an anatomical cross section of the anal canal illustrating a hemorrhoidal condition.

FIG. 3 is a simplified anatomical cross section of the anal canal 32 connected to the rectum 34. Located in anal canal 32 are dilated veins 36, commonly referred to as hemorrhoids or piles. Located at the top of the anal canal 32 is the internal sphincter muscle 38 and the external sphincter muscle 40, the latter of which is voluntary while the prior is involuntary.

OPERATION

Figure 4:
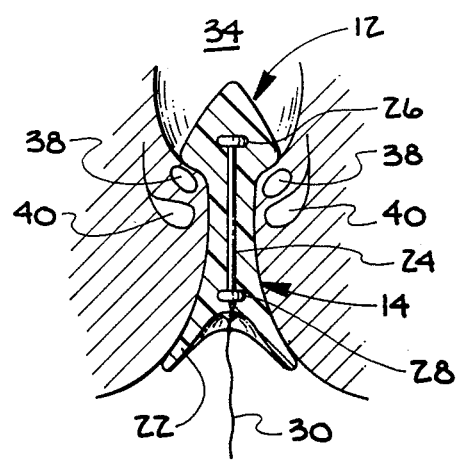
FIG. 4 is a similar anatomical cross section with the hemorrhoidal pessary in place.

The pessary 10 is used in conjunction with an anesthetic ointment which can be applied directly to the anal canal or to the surface of the pessary 10. Before inserting the device 10, if the hemorrhoids are extending from the anal canal, they are gently pushed inward with the index finger. The pessary 10 is then inserted into the anal canal with pressure on the end surface 44 until it can be detected that the corona portion 18 of the head has passed inside the sphincter muscles 38 and 40, as illustrated in FIG. 4. The flange 22 not only inhibits complete insertion but also helps to contain and support the hemorrhoids. After a few minutes, the internal sphincter muscle 38 will grasp the shaft 14 of the device. Due to the very soft and pliable nature of the device 10, the flange 22 can readily deflect to conform to the body shape so as to minimize the discomfort to the wearer. The device 10, which can be worn for four to six hours or longer while sitting, standing or walking, exerts a gentle pressure on the dilated veins, in a similar nature to support hose which compress varicose veins, whereby the degree of swelling and pain can be reduced to relieve the hemorrhoid condition.

To remove the device 10, the withdrawal string 30 is pulled gently until the internal sphincter muscle 38 relaxes and passes the head 12 of the device.

The body 11 of the device can be molded from a variety of soft pliable plastics such as "PLASTISOL", a trademark of the Turnwell Manufacturing Company. A variety of other pliable plastics can be used since sufficient longitudinal rigidity and tensile strength is provided by the internal stiffener 22.

Having described the invention with sufficient clarity and completeness to enable those skilled in the art to make and use the invention, and having set forth the best mode contemplated by the inventor for carrying out his invention, I claim:

1. A hemorrhoidal device insertable in the rectum and held in place by the sphincter muscles comprising:
   a body of molded soft pliable material including a head and shaft portion;
   the head portion having a tapered nose and a corona portion with a circumferential shoulder at the juncture between the head portion and the shaft portion;
   the shaft portion being tapered outward from the head, and the end of the shaft portion terminates in an annular outwardly extending flange;
   a longitudinal stiffener member concentrically positioned within the body of the device and extending longitudinally from the head to approximately the end of the shaft portion; and
   removal means attached to the device for removal of the device.

2. A hemorrhoidal device as set forth in claim 1, wherein the shaft portion is tapered outward from the head to the flange and the diameter of the shaft portion at the juncture with the head is approximately (½) one-half the diameter of the corona portion.

3. A hemorrhoidal device as set forth in claim 1 wherein the stiffener includes enlarged end portions at each end thereof.

4. A hemorrhoidal device as set forth in claim 1, wherein the stiffener member is a thin molded rod of semirigid plastic having enlarged end portions at each end thereof.

5. A hemorrhoidal device as set forth in claim 1, wherein the removal means is a string attached to the stiffener member.

6. A hemorrhoidal device as set forth in claim 1, wherein the circumferential shoulder meets the shaft portion at an angle between approximately ninety degrees (90°) and one hundred thirty degrees (130°).

7. A hemorrhoidal device as set forth in claim 1, wherein the stiffener member is molded within the body of the device to provide the device with sufficient longitudinal rigidity for insertion and tensile strength for removal.

8. A hemorrhoidal device as set forth in claim 2, wherein the extending flange has a higher degree of lateral flexibility than the other portions of the device.

9. A hemorrhoidal device as set forth in claim 1, wherein the shaft portion is tapered outward from the head to the flange and the diameter of the shaft portion at the juncture with the head is approximately (½) one-half the diameter of the corona portion while the diameter of the shaft at the juncture with the flange is approximately the diameter of the corona portion.

10. A hemorrhoidal device as set forth in claim 1, wherein the length of the shaft portion is approximately three times the diameter of the shaft at the juncture with the head.

* * * * *